United States Patent [19]

Yoshida et al.

[11] Patent Number: 5,059,427

[45] Date of Patent: Oct. 22, 1991

[54] PHARMACEUTICAL PREPARATION FOR PERCUTANEOUS ADMINISTRATION CONTAINING EPERISONE OR TOLPERISONE OR SALT THEREOF

[75] Inventors: Mitsuhiro Yoshida, Fukaya; Yutaka Morita, Honjou; Yoshio Ishino, Kumagaya; Shigemitsu Ohsawa, Honjou, all of Japan

[73] Assignees: Sansho Co., Ltd.; Eisai Co., Ltd., both of Tokyo, Japan

[21] Appl. No.: 193,713

[22] Filed: May 13, 1988

[30] Foreign Application Priority Data

May 15, 1987 [JP] Japan .................. 62-118660
Mar. 16, 1988 [JP] Japan .................. 63-62944

[51] Int. Cl.$^5$ .................. A61K 9/06; A61K 47/12; A61K 31/41; C07D 207/06
[52] U.S. Cl. .................. 424/449; 514/428; 514/784; 514/785; 514/906; 548/571
[58] Field of Search .................. 424/449; 514/784, 785, 514/428, 786, 315, 906; 548/571

[56] References Cited

U.S. PATENT DOCUMENTS

| | | | |
|---|---|---|---|
| 4,637,930 | 1/1987 | Konno et al. | 424/449 |
| 4,638,009 | 1/1987 | Itho et al. | 514/428 |
| 4,695,465 | 9/1987 | Kigasawa et al. | 424/449 |
| 4,746,515 | 5/1988 | Cheng et al. | 424/449 |

FOREIGN PATENT DOCUMENTS

| | | |
|---|---|---|
| 1518683 | 7/1978 | United Kingdom . |
| 2122087 | 1/1984 | United Kingdom . |

*Primary Examiner*—Merrell C. Cashion, Jr.
*Assistant Examiner*—Carlos Azpuru
*Attorney, Agent, or Firm*—Flynn, Thiel, Boutell & Tanis

[57] ABSTRACT

A pharmaceutical preparation for the percutaneous administration comprises eperisone or tolperisone, including salts thereof, and a monoglyceride of an aliphatic acid having 8 to 12 carbon atoms or/and an ester of lactic acid with an aliphatic alcohol having 12 to 18 carbon atoms. It is improved in the percutaneous absorption.

10 Claims, 4 Drawing Sheets

PHARMACEUTICAL PREPARATION FOR PERCUTANEOUS ADMINISTRATION CONTAINING EPERISONE OR TOLPERISONE OR SALT THEREOF

The present invention relates to a pharmaceutical preparation for percutaneous administration containing eperisone or tolperisone or a salt thereof and, more particularly, to a pharmaceutical preparation for percutaneous administration containing eperisone or tolperisone or a salt which exhibits excellent skin penetration.

PRIOR ART

Eperisone or tolperisone, or salts thereof, are known as agents for improving not only various symptoms with respect to spastic paralysis but also muscle tonus derived from diseases such as cervical syndrome, inflammation of the circumference of humeral joints, and low back pain. At the present time, these pharmaceutical preparations containing eperisone or tolperisone, or a salt thereof, are orally administered.

However, if percutaneous administration of a pharmaceutical preparation is possible, it is desired to adopt percutaneous administration rather than oral administration because percutaneous administration can avoid not only a first-pass effect but also damage to gastrointestinal tracts. For this reason, extensive and intensive studies were conducted with a view to developing a method of administration other than oral administration, e.g., percutaneous administration, with respect to eperisone or tolperisone or a salt thereof, as well as studying the possibility of the preparation of percutaneously absorbable pharmaceutical preparations of which persistence of systemic action and development of local action can be expected.

In order to prepare percutaneously absorbable pharmaceutical preparations from eperisone or tolperisone or a salt thereof, it is necessary that eperisone or tolperisone, or a salt thereof, have excellent solubility and that a base capable of improving the skin penetration of eperisone or tolperisone or a salt thereof be used. The present inventors have made extensive and intensive studies with a view to finding these bases.

SUMMARY OF THE INVENTION

The present inventors have found through their studies that a monoglyceride of an aliphatic acid having 8 to 12 carbon atoms or/and an ester of lactic acid with an aliphatic alcohol having 12 to 18 carbon atoms can not only dissolve eperisone or tolperisone, or a salt thereof, better than other bases do but also remarkably improves the skin penetration of eperisone or tolperisone or a salt thereof, which led to the completion of the present invention.

Accordingly, the present invention provides a pharmaceutical preparation for percutaneous administration containing eperisone or tolperisone, or a salt thereof, which comprises eperisone or tolperisone, or a salt thereof, and a monoglyceride of an aliphatic acid having 8 to 12 carbon atoms or/and an ester of lactic acid with an aliphatic alcohol having 12 to 18 carbon atoms blended therewith.

The invention provides a pharmaceutical preparation for percutaneous administration which comprises (a) eperisone, a salt thereof, tolperisone or a salt thereof and (b) a monoglyceride of an aliphatic acid having 8 to 12 carbon atoms or/and an ester of lactic acid with an aliphatic alcohol having 12 to 18 carbon atoms.

It is preferable that the weight ratio of (a) to (b) ranges from 1/0.1 to 1/500 and the preparation comprises 0.1 to 10 wt. % of (a), 1 to 50 wt. % of (b) and the balance being a pharmacologically acceptable carrier.

It is preferable that (b) is glycerin monocaprylate. It is also preferable that (a) is a hydrochloric acid salt of eperisone and (b) is a monoglyceride of an aliphatic acid having 8 to 12 carbon atoms in combination. Preferable aliphatic alcohols for (b) include myristyl alcohol, cetyl alcohol and lauryl alcohol.

The invention provides the preparation with an unexpected improvement with respect to percutaneous absorption.

Examples of the monoglyceride of an aliphatic acid having 8 to 12 carbon atoms used in the present invention include glycerin monocaprylate, glycerin monocaprate, and glycerin monolaurate, among which glycerin monocaprylate is particularly preferable.

Examples of the ester of lactic acid with an aliphatic alcohol having 12 to 18 carbon atoms include myristyl lactate, cetyl lactate, and lauryl lactate.

In the pharmaceutical preparation of the present invention, the total amount of blending of the monoglyceride of an aliphatic acid having 8 to 12 carbon atoms or/and the ester of lactic acid with an aliphatic alcohol having 12 to 18 carbon atoms is preferably 0.1 to 500 by weight, based on eperisone or tolperisone or a salt thereof. The content of eperisone or tolperisone, or a salt thereof, in the pharmaceutical preparation is preferably 0.1 to 10% by weight, while the total amount of blending of the monoglyceride of an aliphatic acid having 8 to 12 carbon atoms or/and the ester of lactic acid with an aliphatic alcohol having 12 to 18 carbon atoms is preferably 1 to 50% by weight, based on the pharmaceutical preparation.

There is no particular limitation with respect to the form of the pharmaceutical preparation of the present invention, and the pharmaceutical preparation may be in the form of any of ointments, creams, patches, lotions, etc.

All the base ingredients which are commonly used as pharmaceutical preparations for percutaneous administration may be used as base ingredients in addition to the monoglyceride of an aliphatic acid having 8 to 12 carbon atoms or/and the ester of lactic acid with an aliphatic alcohol having 12 to 18 contained in the pharmaceutical preparation of the present invention, and any of oleaginous base ingredients and aqueous base ingredients may be used. Examples of oleaginous base ingredients include white petrolatum, purified lanolin, squalane, silicone, liquid paraffin, vegetable oils, and waxes. Examples of aqueous base ingredients include water, lower alcohols, polyhydric alcohols, and water-soluble polymers. Examples of base ingredients, e.g., polymer compositions, which are commonly used for the patch include those exhibiting tuckiness, such as natural rubbers, synthetic rubbers, styrene-isoprene-styrene block copolymers (SIS), polyacrylate resins, and polyisobutylene resins; soft polyamide resins; polyvinyl alcohol; and polyacrylic resins.

Besides the above-described components, the pharmaceutical composition of the present invention may optionally contain surfactants, stabilizers, preservatives, and antiseptics which are used in known pharmaceutical preparations for percutaneous administration.

The pharmaceutical preparation of the present invention has the following advantages.

(1) The availability is high because it is free from a fast-pass effect.
(2) It causes no damage to gastrointestinal tracts.
(3) Its action is persistent.
(4) The administration can thereof immediately be stopped when adverse reactions (those derived from the drug effect of eperisone or tolperisone) are observed.
(5) It can directly be administered to the affected parts (e.g., in the case of stiff shoulder or lumbago).

DESCRIPTION OF THE PREFERRED EMBODIMENT

The present invention will now be described in more detail with reference to not only the following Experimental Examples, which substantiate the effect of a monoglyceride of an aliphatic acid having 8 to 12 carbon atoms or/and an ester of lactic acid with an aliphatic alcohol having 12 to 18 carbon atoms on the skin penetration of eperisone or tolperisone, or a salt thereof, but also Examples of the present invention, which should not be construed as limiting the scope of the present invention.

EXPERIMENTAL EXAMPLE 1

The following various test samples were prepared to conduct experiments on skin penetration in vitro according to the following method.

The results are shown in Table 1.

Preparation of test samples

Sample 1 of the present invention:

Glycerin mono-dicaprylate (comprising glycerin monocaprylate and glycerin dicaprylate in a weight ratio of 1:1; Homotex PT ®; a product of Kao Corp.) was used as a base, and eperisone hydrochloride was suspended in the base to prepare a sample (containing 280 mg of eperisone hydrochloride in 2 g of the sample).

Comparative sample 1:

Propylene glycol was used as a base, and eperisone hydrochloride was suspended in the base to prepare a sample (containing 334 mg of eperisone hydrochloride in 2 g of the sample).

Comparative sample 2:

1,3-Butylene glycol was used as a base, and eperisone hydrochloride was suspended in the base to prepare a sample (containing 182 mg of eperisone hydrochloride in 2 g of the sample).

Comparative sample 3:

Dipropylene glycol was used as a base, and eperisone hydrochloride was suspended in the base to prepare a sample (containing 124 mg of eperisone hydrochloride in 2 g of the sample).

Method of experiment on skin penetration in vitro

Abdominal hair of a male Wistar rat weighing about 230 g (8- to 9-week old) was removed under anesthesia. After 24 hr, the rat was similarly anesthetized to confirm that the skin was free from a wound. Then, the skin was cleanly wiped with 70% ethanol, followed by ablation of the entire skin of the abdomen.

The ablated skin was fixed to the lid of a horizontal membrane type in-vitro diffusion cell having a permeation area of 7.54 $cm^2$ in such a manner that the skin side served as a donor surface. 50 ml of a phosphate buffer having a pH value of 7.4 was used as a receiver solution 2 g of the sample solution was dropped and applied to the donor side. The lid was carefully fixed to the receptor so that no air bubbles remained on the dermis side, followed by incubation in an incubator of 32° C. The receptor solution was stirred with a stirrer and sampled in an amount of 0.5 ml at predetermined time intervals to quantitatively determine eperisone hydrochloride. The quantitative determination was conducted by high-performance liquid chromatography.

Figure 1:
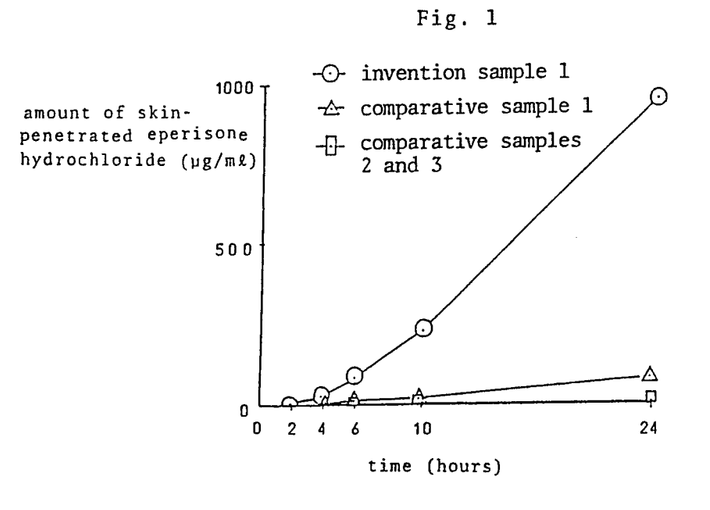
FIGS. 1 to 7 are graphs showing the results of experiments on skin penetration in vitro in Experimental Examples 1 to 7, respectively.

As can be seen from the results shown in FIG. 1, the skin penetration of eperisone hydrochloride when glycerin mono-dicaprylate was used as the base ingredient was remarkably excellent and about 10 times as high as that when propylene glycol was used as the base ingredient and about 200 times as high as those when 1,3-butylene glycol and dipropylene glycol were used each as the base ingredient.

EXPERIMENTAL EXAMPLE 2

The following test samples were prepared to conduct experiments on skin penetration in vitro in the same manner as that of Experimental Example 1.

Figure 2:
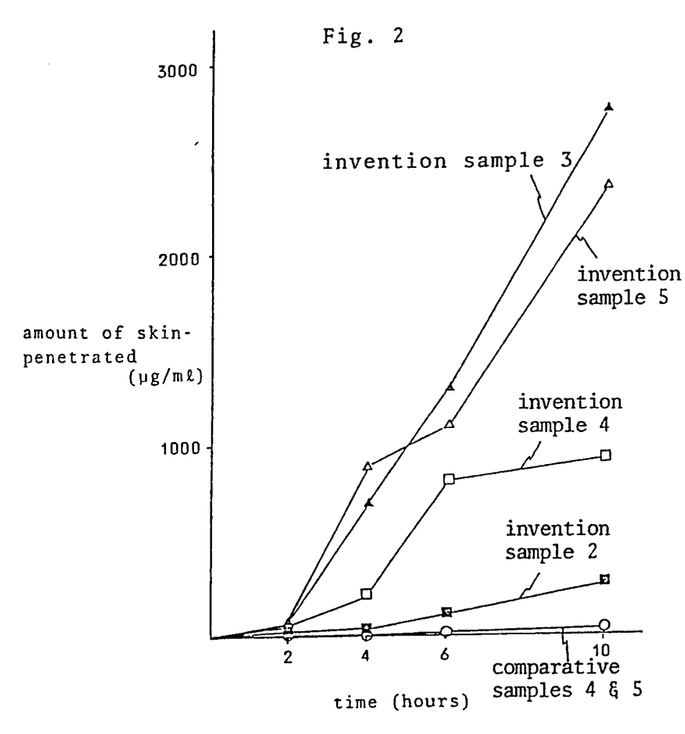

The results are shown in FIG. 2.

Preparation of test samples

Sample 2 of the present invention:

A propylene glycol dicaprylate solution containing 10% by weight of Homotex PT ® was used as a base, and eperisone hydrochloride was suspended in the base to prepare a sample (containing 45.6 mg of eperisone hydrochloride in 2 g of the sample).

Sample 3 of the present invention:

A propylene glycol solution containing 10% by weight of cetyl lactate was used as a base, and eperisone hydrochloride was suspended in the base to prepare a sample (containing 400 mg of eperisone hydrochloride in 2 g of the sample).

Sample 4 of the present invention:

A propylene glycol dicaprylate solution containing 10% by weight of Homotex PT ® was used as a base, and tolperisone hydrochloride was suspended in the base to prepare a sample (containing 86 mg of tolperisone hydrochloride in 2 g of the sample).

Sample 5 of the present invention:

A propylene glycol solution containing 10% by weight of cetyl lactate was used as a base, and tolperisone hydrochloride was suspended in the base to prepare a sample (containing 484 mg of tolperisone hydrochloride in 2 g of the sample).

Comparative sample 4:

Propylene glycol was used as a base, and eperisone hydrochloride was suspended in the base to prepare a sample (containing 280 mg of eperisone hydrochloride in 2 g of the sample).

Comparative sample 5:

Propylene glycol was used as a base, and tolperisone hydrochloride was suspended in the base to prepare a sample (containing 484 mg of tolperisone hydrochloride in 2 g of the sample).

As can be seen from the results shown in FIG. 2, the skin penetration of eperisone hydrochloride or tolperisone hydrochloride, when a solution containing a monoglyceride of an aliphatic acid having 8 to 12 carbon atoms or an ester of lactic acid with an aliphatic alcohol having 12 to 18 carbon atoms was used as the base ingredient, was remarkably superior to that when only propylene glycol was used as the base ingredient.

EXPERIMENTAL EXAMPLE 3

The following various test samples were prepared to conduct experiments on skin penetration in vitro in the same manner as that of Experimental Example 1.

Figures 3, 4:
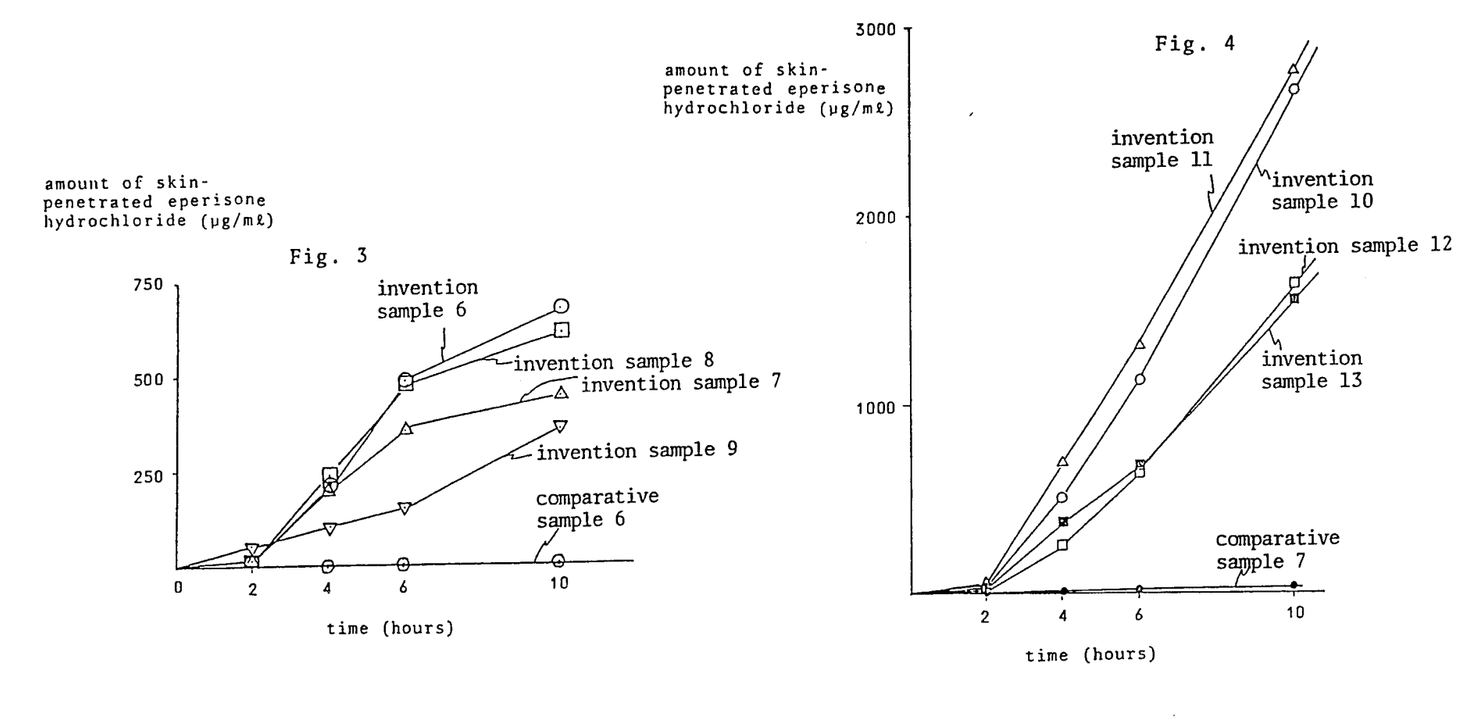

The results are shown in FIG. 3.

Preparation of test samples

Sample 6 of the present invention:

A propylene glycol dicaprylate solution containing 10% by weight of glycerin monocaprylate was used as a base, and eperisone hydrochloride was suspended in the base to prepare a sample (containing 90 mg of eperisone hydrochloride in 2 g of the sample).

Sample 7 of the present invention:

A propylene glycol dicaprylate solution containing 10% by weight of glycerin monocaprate was used as a base, and eperisone hydrochloride was suspended in the base to prepare a sample (containing 90 mg of eperisone hydrochloride in 2 g of the sample).

Sample 8 of the present invention:

A propylene glycol dicaprylate solution containing 10% by weight of glycerin monolaurate was used as a base, and eperisone hydrochloride was suspended in the base to prepare a sample (containing 90 mg of eperisone hydrochloride in 2 g of the sample).

Sample 9 of the present invention:

A propylene glycol solution containing 25% by weight of glycerin mono-dicaprylate (Homotex PT ®; a product of Kao Corp.) was used as a base, and eperisone hydrochloride was suspended in the base to prepare a sample (containing 83.1 mg of eperisone hydrochloride in 2 g of the sample).

Comparative sample 6:

Propylene glycol dicaprylate was used as a base, and eperisone hydrochloride was suspended in the base to prepare a sample (containing 20 mg of eperisone hydrochloride in 2 g of the sample).

As can be seen from the results shown in FIG. 3, the skin penetration of eperisone hydrochloride, when a propylene glycol dicaprylate solution containing a monoglyceride of an aliphatic acid having 8 to 12 carbon atoms was used as the base ingredient, was remarkably superior to that when only propylene glycol dicaprylate was used as the base ingredient.

EXPERIMENTAL EXAMPLE 4

The following various test samples were prepared to conduct experiments on skin penetration in vitro in the same manner as that of Experimental Example 1.

The results are shown in FIG. 4.

Figure 8:
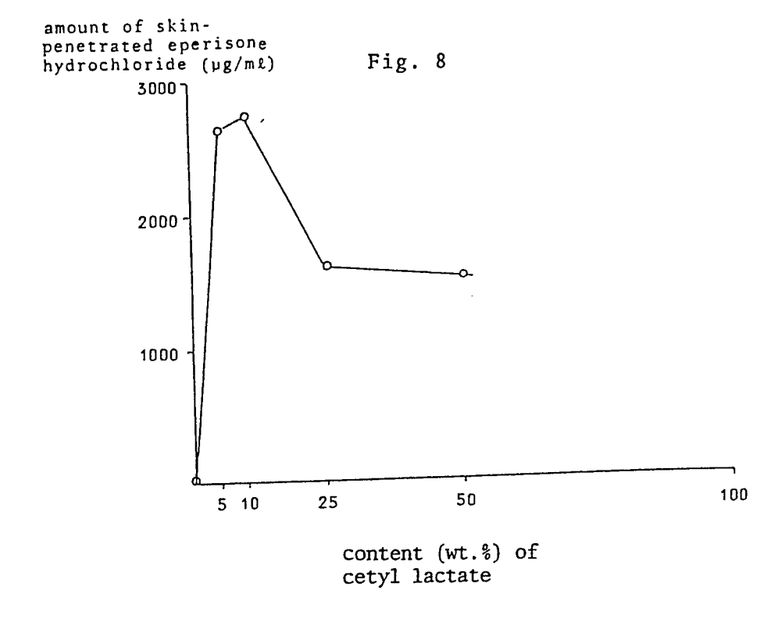
FIG. 8 is a graph prepared by plotting the skin penetration values after a lapse of 10 hr, shown in FIG. 4 against the amount of blending of cetyl lactate.

Further, the skin penetration values after a lapse of 10 hr shown in FIG. 4 were plotted against the amount of blending of cetyl lactate to prepare the graph shown in FIG. 8.

Preparation of test samples

Sample 10 of the present invention:

A propylene glycol solution containing 5% by weight of cetyl lactate was used as a base, and eperisone hydrochloride was suspended in the base to prepare a sample (containing 400 mg of eperisone hydrochloride in 2 g of the sample).

Sample 11 of the present invention:

A propylene glycol solution containing 10% by weight of cetyl lactate was used as a base, and eperisone hydrochloride was suspended in the base to prepare a sample (containing 400 mg of eperisone hydrochloride in 2 g of the sample).

Sample 12 of the present invention:

A propylene glycol solution containing 25% by weight of cetyl lactate was used as a base, and eperisone hydrochloride was suspended in the base to prepare a sample (containing 400 mg of eperisone hydrochloride in 2 g of the sample).

Sample 13 of the present invention:

A propylene glycol solution containing 50% by weight of cetyl lactate was used as a base, and eperisone hydrochloride was suspended in the base to prepare a sample (containing 400 mg of eperisone hydrochloride in 2 g of the sample).

Comparative sample 7:

Propylene glycol was used as a base, and eperisone hydrochloride was suspended in the base to prepare a sample (containing 280 mg of eperisone hydrochloride in 2 g of the sample).

As can be seen from the results shown in FIG. 4, the skin penetration of eperisone hydrochloride, when a propylene glycol solution containing cetyl lactate was used as the base ingredient, was remarkably superior to that when only propylene glycol was used as the base ingredient.

EXPERIMENTAL EXAMPLE 5

The following various test samples were prepared to conduct experiments on skin penetration in vitro in the same manner as that of Experimental Example 1.

Figure 5:
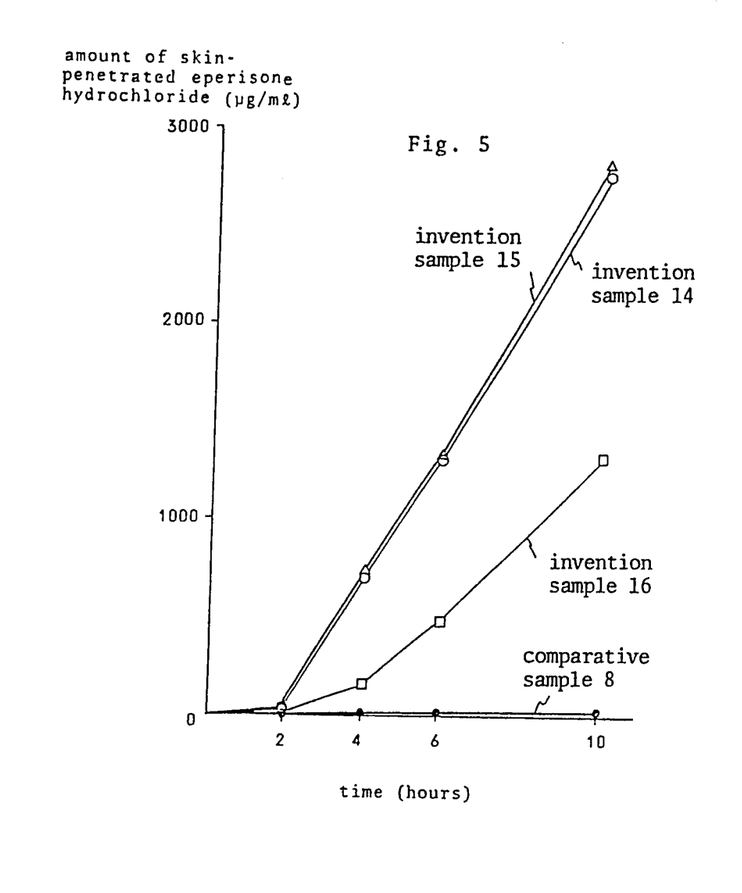

The results are shown in FIG. 5.

Preparation of test samples

Sample 14 of the present invention:

A propylene glycol solution containing 10% by weight of cetyl lactate was used as a base, and eperisone hydrochloride was suspended in the base to prepare a sample (containing 400 mg of eperisone hydrochloride in 2 g of the sample).

Sample 15 of the present invention:

A propylene glycol solution containing 10% by weight of myristyl lactate was used as a base, and eperisone hydrochloride was suspended in the base to prepare a sample (containing 440 mg of eperisone hydrochloride in 2 g of the sample).

Sample 16 of the present invention:

A propylene glycol solution containing 10% by weight of lauryl lactate was used as a base, and eperisone hydrochloride was suspended in the base to prepare a sample (containing 400 mg of eperisone hydrochloride in 2 g of the sample).

Comparative sample 8:

Propylene glycol was used as a base, and eperisone hydrochloride was suspended in the base to prepare a sample (containing 280 mg of eperisone hydrochloride in 2 g of the sample).

As can be seen from the results shown in FIG. 5, the skin penetration of eperisone hydrochloride, when a propylene glycol solution containing an ester of lactic acid with an aliphatic alcohol having 12 to 18 carbon atoms was used as the base ingredient, was remarkably superior to that when only propylene glycol was used as the base ingredient.

EXPERIMENTAL EXAMPLE 6

The following various test samples were prepared to conduct experiments on skin penetration in vitro in the same manner as that of Experimental Example 1.

Figure 6:
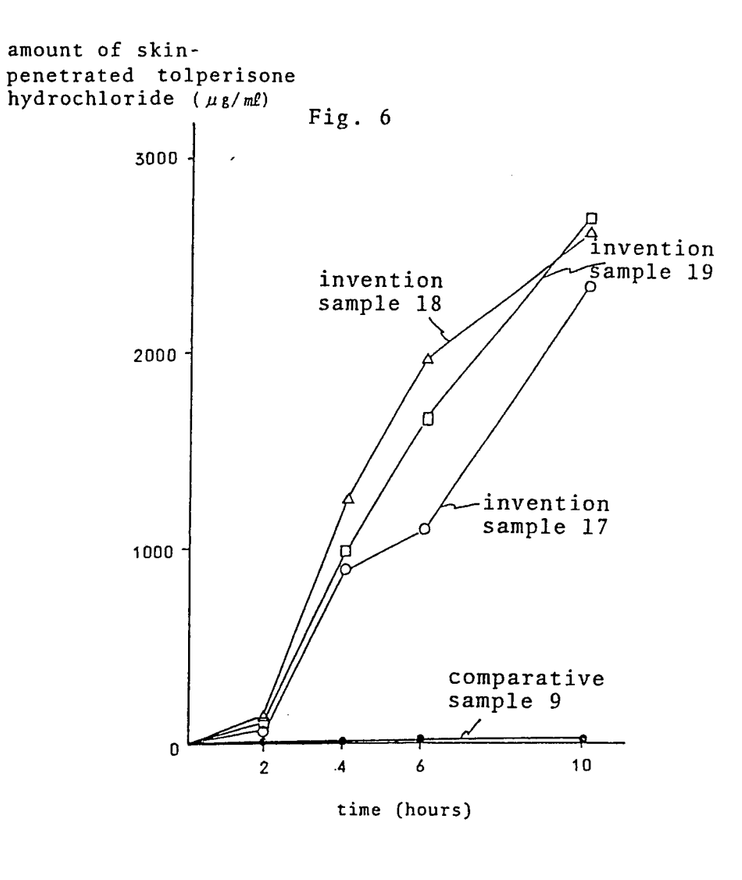

The results are shown in FIG. 6.

Preparation of test samples

Sample 17 of the present invention:

A propylene glycol solution containing 10% by weight of cetyl lactate was used as a base, and tolperisone hydrochloride was suspended in the base to prepare a sample (containing 484 mg of tolperisone hydrochloride in 2 g of the sample).

Sample 18 of the present invention:

A propylene glycol solution containing 10% by weight of myristyl lactate was used as a base, and tolperisone hydrochloride was suspended in the base to prepare a sample (containing 462 mg of tolperisone hydrochloride in 2 g of the sample).

Sample 19 of the present invention:

A propylene glycol solution containing 10% by weight of lauryl lactate was used as a base, and tolperisone hydrochloride was suspended in the base to prepare a sample (containing 462 mg of tolperisone hydrochloride in 2 g of the sample).

Comparative sample 9:

Propylene glycol was used as a base, and tolperisone hydrochloride was suspended in the base to prepare a sample (containing 484 mg of tolperisone hydrochloride in 2 g of the sample).

As can be seen from the results shown in FIG. 6, the skin penetration of tolperisone hydrochloride when a propylene glycol solution containing an ester of lactic acid with an aliphatic alcohol having 12 to 18 carbon atoms was used as the base ingredient, was remarkably superior to that when only propylene glycol was used as the base ingredient.

EXPERIMENTAL EXAMPLE 7

Homotex PT ® was blended in various amounts to examine the effect of the amount of blending of Homotex PT ® (glycerin monocaprylate) on the skin penetration of eperisone hydrochloride in the same manner as that of Experimental Example 1.

Figure 7:
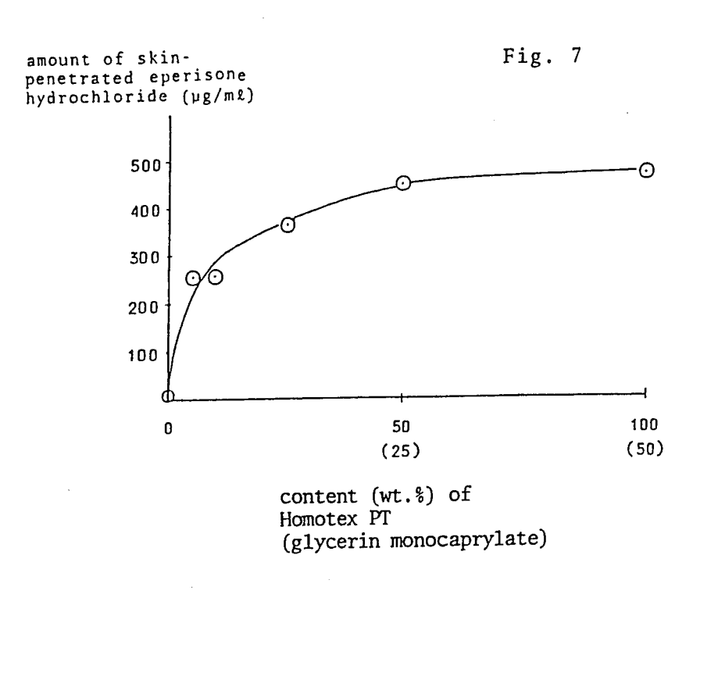

The results are shown in FIG. 7. The ordinate of FIG. 7 represents the amount of skin penetration after 10 hr.

As can be seen from FIG. 7, when compared with the sample free from having Homotex PT ® blended therewith, the sample containing 5% by weight of Homotex PT ® blended therewith (amount of blending of glycerin monocaprylate: 2.5% by weight) and the sample containing 100% by weight of Homotex PT ® blended therewith (amount of blending of glycerin monocaprylate: 50% by weight) exhibited excellent skin penetration of eperisone hydrochloride, i.e., an about 80-fold increase and an about 140-fold increase in the skin penetration of eperisone hydrochloride, respectively.

EXAMPLE 1

(oleaginous ointment)

Glycerin mono-dicaprylate (Homotex PT ®) was heated at 60° C. and eperisone hydrochloride was added thereto, followed by stirring to prepare a homogeneous mixture. Separately, sorbitan trioleate and white petrolatum were heated at 60° C. to homogeneously mix them with each other. The above homogeneous mixture, prepared by stirring of glycerin mono-dicaprylate and eperisone hydrochloride, was added thereto. All of them were stirred to homogeneously mix them with each other. The mixture was allowed to cool at room temperature, thereby preparing an oleaginous ointment having the following composition:

| | |
|---|---|
| eperisone hydrochloride | 1.5% by weight |
| glycerin mono-dicaprylate (Homotex PT ®) | 5% by weight |
| sorbitan trioleate | 3% by weight |
| white petrolatum | 90.5% by weight |

EXAMPLE 2

(hydrophilic ointment)

Glycerin monocaprylate, polyoxyethylene(20) sorbitan monooleate, macrogol ointment prescribed in the Pharmacopoeia of Japan and a preservative were heated at 60° C. and homogeneously mixed with each other, followed by addition of a finely divided powder of eperisone hydrochloride. They were sufficiently mixed with each other while cooling, thereby preparing a hydropholic ointment having the following composition:

| | |
|---|---|
| eperisone hydrochloride | 2% by weight |
| glycerin monocaprylate | 3% by weight |
| polyoxyethylene (20) sorbitan monooleate | 2% by weight |
| macrogol ointment prescribed in the Pharmacopoeia of Japan | 92.9% by weight |
| preservative | 0.1% by weight |

EXAMPLE 3

(O/W type cream)

Squalane, isopropyl myristate, stearic acid, glycerin monostearate, sorbitan monopalmitate, polyoxyethylene(20) sorbitan monostearate, and glycerin monocaprylate were heated at 70° C. for homogeneous dissolution. Eperison hydrochloride was added to the resulting solution, followed by stirring to prepare a homogeneous mixture. Propylene glycol, a preservative, purified water heated at 60° C. was gradually added thereto. The resulting mixture was allowed to cool at 30° C. while stirring, thereby preparing an O/W type cream having the following composition:

| | |
|---|---|
| eperisone | 2% by weight |
| squalane | 8% by weight |
| isopropyl myristate | 4% by weight |
| stearic acid | 4% by weight |
| glycerin monostearate | 4% by weight |
| sorbitan monopalmitate | 1.5% by weight |
| polyoxyethylene (20) sorbitan monostearate | 1.5% by weight |
| glycerin monocaprylate | 5% by weight |
| propylene glycol | 5% by weight |
| preservative | 0.1% by weight |
| purified water | 64.9% by weight |

EXAMPLE 4

(oleaginous ointment)

Glycerin monolaurate and glycerin monocaprylate were heated at 55° C., and eperisone hydrochloride were added thereto to prepare a homogeneous mixture. This homogeneous mixture was added to a mixture of octyldodecyl myristate, sorbitan sesquioleate, purified lanolin, propylene glycol monostearate, and white petrolatum heated to 70° C. to prepare a homogeneous mixture and then allowed to cool while stirring, thereby preparing an oleaginous ointment having the following composition:

| | |
|---|---|
| eperisone hydrochloride | 1% by weight |
| glycerin monolaurate | 3% by weight |
| glycerin monocaprylate | 3% by weight |
| octyldodecyl myristate | 10% by weight |
| sorbitan sesquioleate | 5% by weight |
| purified lanolin | 10% by weight |
| propylene glycol monostearate | 2% by weight |
| white petrolatum | 66% by weight |

EXAMPLE 5

(oleaginous ointment)

Propylene glycol was heated at 60° C., and eperisone hydrochloride was added and dissolved therein. Cetyl lactate and Plastibase (trademark of a product of Squibb Japan Inc., a mixture of 95% by weight of liquid paraffin with 5% by weight of polyethylene having a molecular weight of 10,000 to 30,000) heated to 60° C. to prepare a mixture was added to the resulting solution. The resulting mixture was allowed to cool at room temperature while stirring, thereby preparing an oleaginous ointment having the following composition:

| | |
|---|---|
| eperisone | 5% by weight |
| cetyl lactate | 10% by weight |
| propylene glycol | 15% by weight |
| Plastibase | 70% by weight |

EXAMPLE 6

(oleaginous ointment)

Cetostearyl alcohol and myristyl lactate were added to white petrolatum heated to 70° C., followed by mixing and dissolution. To the solution was added a solution prepared by heating 1,3-butylene glycol to 70° C. and dissolving purified soybean lecithin and tolperisone hydrochloride in the heated butylene glycol. They were mixed with each other with a homomixer. The resulting mixture was allowed to cool while stirring to prepare an ointment having the following composition:

| | |
|---|---|
| tolperisone | 7% by weight |
| myristyl lactate | 15% by weight |
| 1,3-butylene glycol | 15% by weight |
| cetostearyl alcohol | 7% by weight |
| purified soybean lecithin | 2% by weight |
| white petrolatum | 54% by weight |

EXAMPLE 7

(oleaginous ointment)

Propylene glycol was heated to 70° C., and eperisone hydrochloride, Homotex PT, cetyl lactate, cetostearyl alcohol, stearic acid, and propylene glycol monostearate were added and dissolved therein. The resulting solution was added to Plastibase heated to 70° C., followed by kneading and mixing. The resulting mixture was allowed to cool while stirring, thereby preparing an ointment having the following composition:

| | |
|---|---|
| eperisone hydrochloride | 10% by weight |
| glycerin mono-dicaprylate (Homotex PT ®) | 5% by weight |
| cetyl lactate | 10% by weight |
| cetostearyl alcohol | 3% by weight |
| stearic acid | 3% by weight |
| propylene glycol monostearate | 8% by weight |
| propylene glycol | 25% by weight |
| Plastibase | 36% by weight |

EXAMPLE 8

(oleaginous ointment)

White petrolatum was heated at 70° C., and purified lanolin, glycerin monocaprate, and tolperisone hydrochloride were added thereto, followed by kneading while cooling, thereby preparing an ointment having the following composition:

| | |
|---|---|
| tolperisone | 10% by weight |
| glycerin monocaprate | 8% by weight |
| purified lanolin | 20% by weight |
| white petrolatum | 62% by weight |

EXAMPLE 9

(oleaginous ointment)

Plastibase was heated to 70° C. and kneaded with cetostearyl alcohol, propylene glycol monostearate, cetyl lactate, and myristyl lactate, Propylene glycol containing tolperisone hydrochloride suspended therein was added to the above mixture, followed by kneading while cooling, thereby preparing an ointment having the following composition:

| | |
|---|---|
| tolperisone | 5% by weight |
| cetyl lactate | 7.5% by weight |
| myristyl lactate | 7.5% by weight |
| propylene glycol | 10% by weight |
| propylene glycol monostearate | 2% by weight |
| cetostearyl alcohol | 3% by weight |
| Plastibase | 65% by weight |

EXAMPLE 10

(patch)

A solution prepared by heating a mixture of SIS rubber, Alcohol P-100 ® (alicyclic petroleum resin) and liquid paraffin to 130° C. was mixed with a solution prepared by heating eperisone hydrochloride, Homotex PT ®, cetyl lactate, glycerin monooleate, and dibutyl hydroxytoluene to 70° C. The resulting mixture was applied and extended on a suitable support, thereby preparing a patch having the following composition:

| | |
|---|---|
| SIS rubber | 35% by weight |
| Alcohol P-100 ® | 24% by weight |
| liquid paraffin | 18% by weight |
| eperisone hydrochloride | 2% by weight |
| Homotex PT ® | 10% by weight |

-continued

| | | |
|---|---|---|
| cetyl lactate | 5% | by weight |
| glycerin monooleate | 5% | by weight |
| dibutylhydroxytoluene | 1% | by weight |

EXAMPLE 11

(patch)

A solution prepared by heating a mixture of natural rubber, a rosin resin, polybutene, and zinc oxide to 130° C. was mixed with a solution prepared by heating tolperisone hydrochloride, glycerin monocaprate, and propylene glycol to 70° C. The resulting mixture was applied and extended on a suitable support, thereby preparing a patch having the following composition:

| | | |
|---|---|---|
| natural rubber | 32% | by weight |
| rosin resin | 18% | by weight |
| polybutene | 12% | by weight |
| zinc oxide | 18% | by weight |
| tolperisone hydrochloride | 5% | by weight |
| glycerin monocaprate | 10% | by weight |
| propylene glycol | 5% | by weight |

EXAMPLE 12

(gel-form ointment)

1.5 parts by weight of Carbopol 940 ® (carboxyvinyl polymer; a product of Goodrich) was suspended in 15 parts by weight of propylene glycol containing ethylparaben and propylparaben dissolved therein. A suitable amount of purified water was added to the suspension while stirring to prepare a homogeneous slurry. Separately, eperisone hydrochloride, cetyl lactate, and Homotex PT ® were added to 15 parts by weight of propylene glycol. The above-prepared slurry was gradually added to the resulting solution while stirring, thereby preparing a homogeneous gel-form ointment having the following composition:

| | | |
|---|---|---|
| eperisone | 5% | by weight |
| cetyl lactate | 5% | by weight |
| Homotex PT ® | 5% | by weight |
| Carbopol 940 ® | 1.5% | by weight |
| propylene glycol | 30% | by weight |
| ethylparaben | 0.05% | by weight |
| propylparaben | 0.15% | by weight |
| purified water | a suitable amount | |
| total | 100.0% | |

We claim:

1. A pharmaceutical preparation for percutaneous administration which comprises (a) eperisone, a salt thereof, tolperisone or a salt thereof and (b) an ester of lactic acid with an aliphatic alcohol having 12 to 18 carbon atoms.

2. A preparation as claimed in claim 1, in which a weight ratio of (a) to (b) ranges from 1/0.1 to 1/500.

3. A preparation as claimed in claim 1, which comprises 0.1 to 10 wt. % of (a), 1 to 50 wt. % of (b) and the balance of a pharmacologically acceptable carrier.

4. A preparation is claimed in claim 1, in which said aliphatic alcohol is selected from the group consisting of myristyl alcohol, cetyl alcohol and lauryl alcohol.

5. A preparation as claimed in claim 1, in which (a) is tolperisone hydrochloride and (b) is cetyl lactate.

6. A preparation as claimed in claim 1, in which (a) is eperisone hydrochloride and (b) is myristyl lactate.

7. A preparation as claimed in claim 1, in which (a) is eperisone hydrochloride and (b) is lauryl lactate.

8. A preparation as claimed in claim 1, in which (a) is tolperisone hydrochloride and (b) is myristyl lactate.

9. A preparation as claimed in claim 1, in which (a) is tolperisone hydrochloride and (b) is lauryl lactate.

10. A pharmaceutical preparation for percutaneous administration which comprises (a) eperisone, or a salt thereof, and (b) an ester of lactic acid with an aliphatic acid having 12 to 18 carbon atoms.

* * * * *